United States Patent
Onushkin et al.

(10) Patent No.: US 8,068,661 B2
(45) Date of Patent: Nov. 29, 2011

(54) LED INSPECTION APPARATUS AND LED INSPECTION METHOD USING THE SAME

(75) Inventors: Grigory Onushkin, Gyunggi-do (KR); Joong Kon Son, Seoul (KR); Jong Hoon Lim, Gyunggi-do (KR); Sang Su Hong, Gyunggi-do (KR)

(73) Assignee: Samsung LED Co., Ltd., Gyunggi-do (KR)

( * ) Notice: Subject to any disclaimer, the term of this patent is extended or adjusted under 35 U.S.C. 154(b) by 513 days.

(21) Appl. No.: 12/275,581

(22) Filed: Nov. 21, 2008

(65) Prior Publication Data

US 2009/0136120 A1 May 28, 2009

(30) Foreign Application Priority Data

Nov. 23, 2007 (KR) .................. 10-2007-0120487

(51) Int. Cl.
*G06K 9/00* (2006.01)
(52) U.S. Cl. .................. 382/141; 356/237.1; 356/417; 250/461.1
(58) Field of Classification Search .................. None
See application file for complete search history.

(56) References Cited

U.S. PATENT DOCUMENTS

| | | | |
|---|---|---|---|
| 5,440,384 A | 8/1995 | Yamada et al. | |
| 6,714,670 B1 * | 3/2004 | Goldsworthy et al. | 382/149 |
| 2002/0180955 A1 * | 12/2002 | Lin et al. | 356/121 |
| 2003/0193672 A1 | 10/2003 | Okada et al. | |
| 2004/0213449 A1 * | 10/2004 | Safaee-Rad et al. | 382/141 |

FOREIGN PATENT DOCUMENTS

| | | |
|---|---|---|
| JP | 6-97508 | 4/1994 |
| JP | 2003-279326 | 10/2003 |
| JP | 2004-108911 | 4/2004 |

OTHER PUBLICATIONS

Korean Office Action issued in Korean Patent Application No. 10-2007-0120487, mailed Jun. 10, 2009.
Korean Office Action, w/ English translation thereof, issued in Korean Patent Application No. KR 10-2007-0120487 dated Apr. 28, 2011.
J. Lee et al., "InGaN-Based Ultraviolet Emitting Heterostructures With Quaternary AlInGaN Barriers," IEEE Journal of Selected Topics in Quantum Electronics, vol. 9, No. 5, Sep./Oct. 2003, pp. 1239-1245.
M. A. Reshchikov et al., "Luminescence properties of defects in GaN," Journal of Applied Physics, 97, Apr. 15, 2005.
Japanese Office Action, w/ English translation thereof, issued in Japanese Patent Application No. JP 2008-298366 dated Jul. 5, 2011.

* cited by examiner

*Primary Examiner* — Gregory J Toatley
*Assistant Examiner* — Juan D Valentin
(74) *Attorney, Agent, or Firm* — McDermott Will & Emery LLP

(57) ABSTRACT

Disclosed are a light emitting diode (LED) inspection apparatus, which can determine whether an LED has a defect such as leakage current, without making physical contact with the LED being inspected, and an LED inspection method thereof. The LED inspection apparatus includes an ultraviolet emission unit emitting UV light to an LED, an image generation unit generating an image of the LED to which the UV light is emitted, and a control unit obtaining color or intensity information of the LED from the image of the LED and determining, based on the color information, whether the LED is defective.

10 Claims, 4 Drawing Sheets

LED INSPECTION APPARATUS AND LED INSPECTION METHOD USING THE SAME

CROSS-REFERENCE TO RELATED APPLICATIONS

This application claims the priority of Korean Patent Application No. 2007-120487 filed on Nov. 23, 2007, in the Korean Intellectual Property Office, the disclosure of which is incorporated herein by reference.

BACKGROUND OF THE INVENTION

1. Field of the Invention

The present invention relates to a light emitting diode (LED) inspection apparatus and an LED inspection method using the same, and more particularly, to an LED inspection apparatus capable of determining whether an LED being inspected has a defect such as current leakage, without making physical contact with the LED, and an LED inspection method using the same.

2. Description of the Related Art

The recent improvements in luminous efficiency of a light emitting diode (LED) has expanded application fields of the LED from signaling to a lighting unit, a backlight unit (BLU) for a mobile phone, a light source of a large display device such as a liquid crystal display (LCD) and the like. This is due to the small power consumption and the long life of the LED, compared to related art lighting devices such as bulbs and fluorescent lamps.

The LED is manufactured by processes: growing, on a substrate, semiconductor layers of different conductivity types and an active layer activating light emission between the semiconductor layers, and forming an electrode on each of the semiconductor layers. The LED manufactured in this manner undergoes an inspection of its performance such as light-emission efficiency. Among performances being inspected, the leakage current is considered a factor that affects the reliability of an LED product because of its influence on the LED in terms of stability, life and performance deterioration.

To detect the leakage current, a process for inspecting the LED performance on a chip level is inserted in an LED manufacturing process. The equipment used for this inspection is called a prober, which can measure characteristics after a voltage is applied to an LED in a state where an electrical contact has been made between a transparent electrode and a bonding pad. That is, the prober measures an operating current and a voltage of the LED to which the voltage is applied, thereby inspecting electrical characteristics of the LED.

In the prober, an LED to be inspected on a wafer or chip level is fixed on an XY motion stage that can be moved forward, backward, left and right. A microscope is placed above the LED, and a probe serves as an electrode that applies a current/voltage to the LED. When an applied voltage is increased, an operating current of an LED also increases. Therefore, the leakage current causes the operating current to exceed a predetermined value. Thus, determination of a defective LED can be made by comparison with a voltage/current curve of a reference LED.

However, the inspection needs to be performed after the probe serving as an electrode physically contacts an LED to be inspected. The physical contact may damage the LED. If multiple samples are inspected, moving, contacting and measuring need to be repeatedly performed, undesirably increasing the inspection time. Also, an XY motion stage with high precision needs to be used because each sample needs to be moved according to a probe location.

Accordingly, there is a need for an apparatus that can inspect defects of LEDs with high efficiency, without degrading the performance of the LEDs.

SUMMARY OF THE INVENTION

An aspect of the present invention provides a light emitting diode (LED) inspection apparatus, which can determine whether an LED has a defect such as leakage current, without making physical contact with the LED being inspected, and an LED inspection method thereof.

According to an aspect of the present invention, there is provided a light emitting diode (LED) inspection apparatus including: an ultraviolet emission unit emitting UV light to an LED; an image generation unit generating an image of the LED to which the UV light is emitted; and a control unit obtaining color or intensity information of the LED from the image of the LED and determining, based on the color or intensity information, whether the LED is defective.

The image generation unit may be a charge-coupled (CCD) camera. The UV emission unit may be one of a UV laser, a UV LED, a xenon arc lamp, a mercury arc lamp, and a xenon mercury arc lamp.

The LED device may be one of a blue LED, a red LED and a green LED. The control unit may determine that the LED is defective if a color of the LED is yellow or an intensity of the LED is weak.

The LED inspection apparatus may further include an LED support spaced apart from the UV emission unit at a predetermined interval, and supporting the LED. The LED support may be movable.

According to another aspect of the present invention, there is provided a light emitting device (LED) inspection method including: emitting UV light to an LED; generating, at an image generation unit, an image of the LED to which the UV light is emitted; obtaining the image of the LED generated from the image generation unit; calculating color or intensity information of the LED from the image; and determining, based on the color or intensity information, whether the LED is defective.

The LED may be one of a blue LED, a red LED and a green LED. The LED may be determined to be defective if a color of the LED is yellow or an intensity of the LED is weak.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Exemplary embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. In the figures, the dimensions and the shapes of elements are exaggerated for clarity of illustration.

Figure 1:
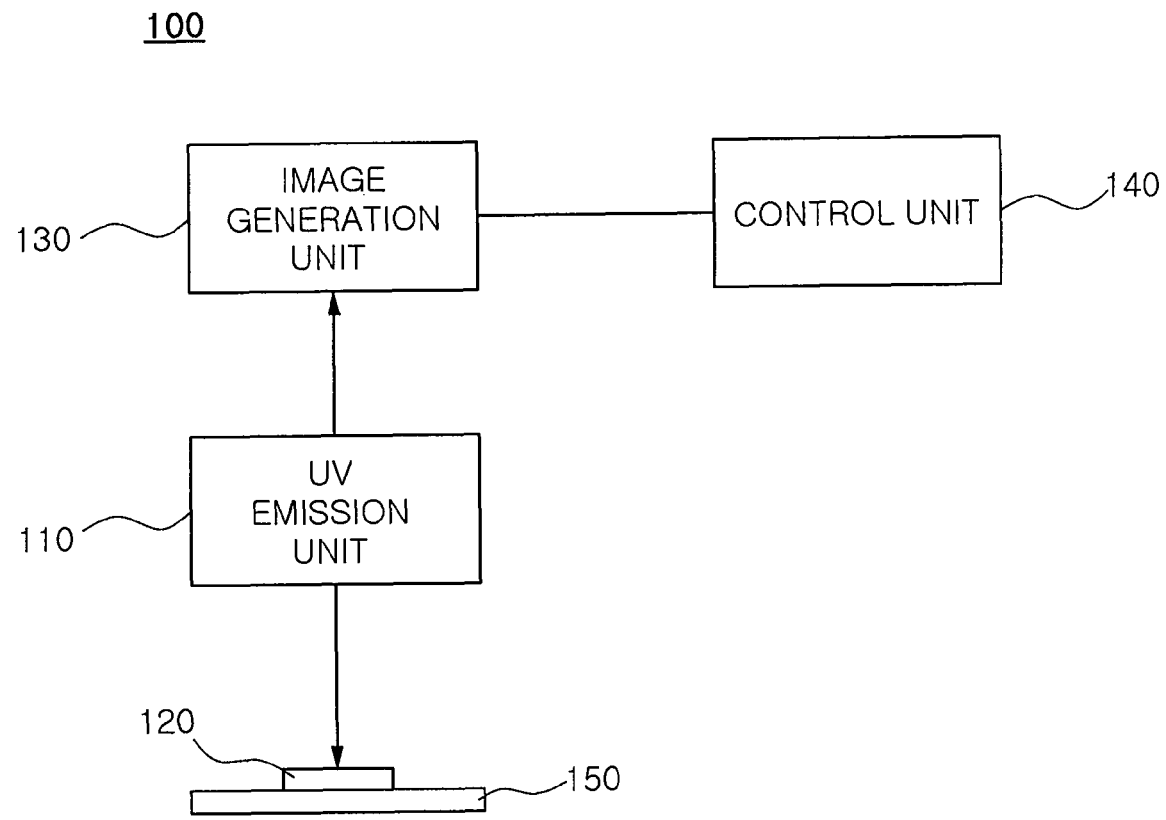
FIG. 1 is a block diagram of an LED inspection apparatus according to an exemplary embodiment of the present invention.

FIG. 1 is a block diagram of a light emitting device (LED) inspection apparatus according to an exemplary embodiment of the present invention. An LED inspection apparatus 100 according to an exemplary embodiment of the present invention includes a UV emission unit 110 emitting ultraviolet (UV) light to an LED 120; an image generation unit 130 generating an image of the LED 120 to which the UV light is emitted; and a control unit 140 obtaining color or intensity information of the LED 120 from the image of the LED 120 generated at the image generation unit 130 and determining, based on the color or intensity information, whether or not the LED 120 is defective.

The UV emission unit 110 emits UV light to the LED 120. The UV emission unit 110 includes a light source that can emit UV light. A UV laser, a UV LED, a xenon arc lamp, a mercury arc lamp, or a xenon mercury arc lamp may be used as the UV emission unit 110. The UV light is emitted to the LED 120 in order to use a photoluminescence effect. When the UV light is emitted to the LED 120, photo-generated carriers are generated in the LED 120 because of energy of the UV light. The photo-generated carriers cause the photoluminescence effect within an active layer and an n-type semiconductor layer.

If the LED 120 has leakage current, light emission caused by the photoluminescence effect in the n-type semiconductor layer occurs dominantly. Hence, light having a predetermined wavelength is generated and thus allows determination of whether the LED 120 is defective. If the LED 120 is not defective (i.e., normal), the photoluminescence effect occurs in both the active layer and the n-type semiconductor layer. In this case, light emission due to the photoluminescence effect in the active layer becomes dominant, and thus light being generated has a different color from the defective LED. This will be described in more detail with reference to FIGS. 2 through 4.

When UV light is emitted to the LED 120, a normal LED and a defective LED generate different colors of light. The image generation unit 130 captures the LEDs to generate an image. To facilitate processing in the control unit 140, the image generation unit 130 may be a charge-coupled (CCD) camera, and the image of the LED 120 captured by the CCD camera may be generated as digital data.

The control unit 140 obtains the image of the LED 120 generated from the image generation unit 130. When the image is obtained, the control unit 140 calculates color or intensity information of the LED 120 to detect a defect based on the color or intensity information. The control unit 140 will be described later in more detail with reference to FIGS. 2 through 5.

The LED inspection apparatus 100 according to this embodiment may further include an LED support 150 spaced apart from the UV emission unit 110 at a predetermined distance and supporting the LED 120. If a plurality of LEDs are placed on a wafer or substrate, the LED support 150 may be movably configured so that UV light can be emitted to an LED 120 which is placed in a desired region.

Figure 2:
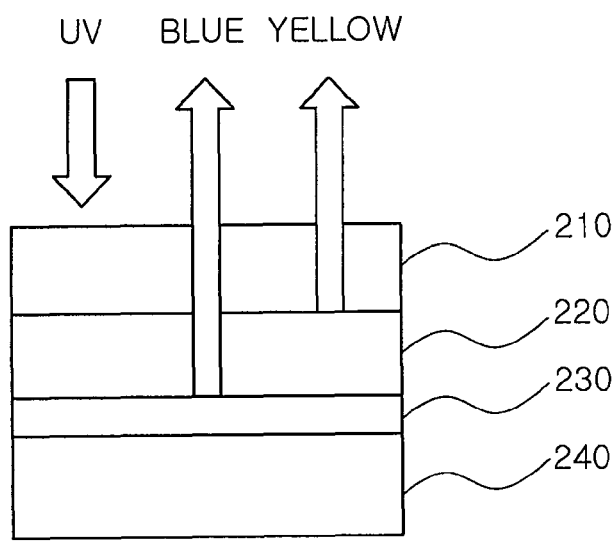
FIG. 2 is a view illustrating light emission when UV light is emitted to a blue LED.

FIG. 2 is a view illustrating light emission when UV light is emitted to a blue LED. The photoluminescence effect refers to an effect in which luminescence occurs when light is emitted to a material such as a semiconductor. The LED of FIG. 2 includes a substrate 210, an n-type semiconductor layer 220, an active layer 230 and a p-type semiconductor layer 240. In the drawing, light emitted from the active layer 230 of the blue LED is extracted to the outside through the substrate 210. FIG. 2 illustrates merely an example of an LED, and the present invention is not limited thereto. It is obvious to those skilled in the art that the LED may include a substrate placed under a p-type semiconductor layer or may include no substrate. According to this embodiment, the substrate 210 may be transparent, considering a direction in which light propagates.

The active layer 230 may include a multi-quantum well (MQW). As shown in FIG. 2, when UV light is emitted to an LED, light of two different colors is generated. In detail, photo-generated carriers are formed by the UV light, causing the photoluminescence effect in the active layer 230 and the n-type semiconductor layer 220. When the LED is a blue LED, blue light is emitted from the active layer, and yellow light is emitted from the n-type semiconductor layer 220. That is, when the UV light is emitted to the blue LED, blue light is emitted from the active layer 230 that is supposed to emit light, while yellow light, not the blue light, is emitted from the n-type semiconductor layer 220, the part excluding the active layer 230. Consequently, if the blue LED is normal, it emits white light, which is the mixed light of blue and yellow light from the active layer 230 and the n-type semiconductor layer 220. This will now be further described with reference to FIGS. 3 and 4.

Figure 3A:
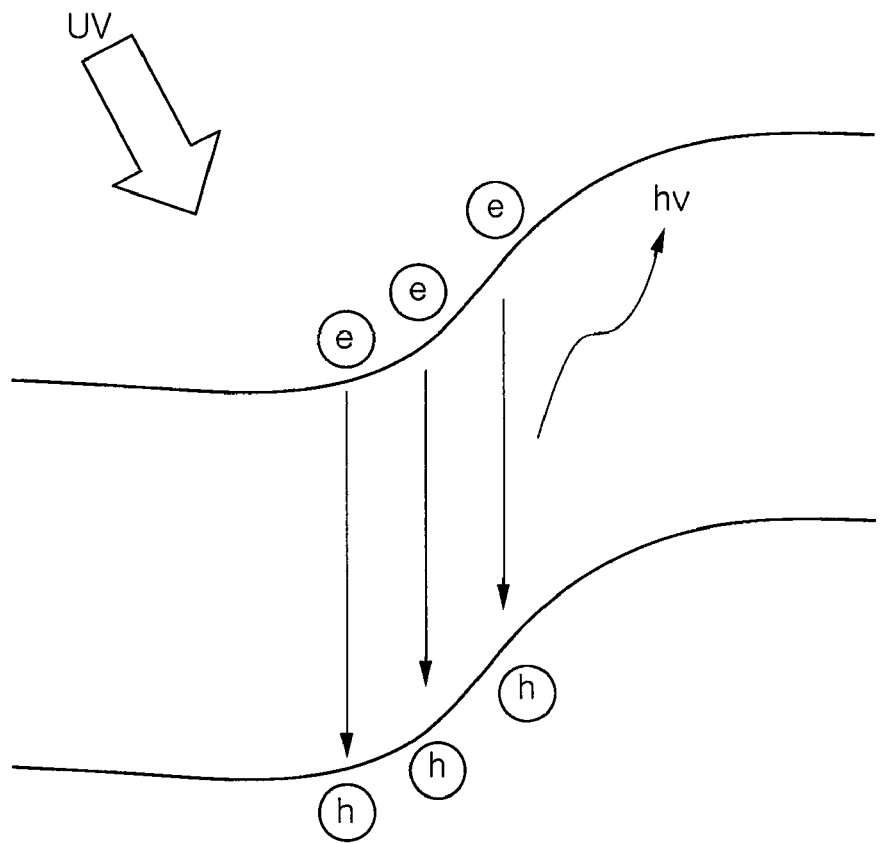
FIG. 3A is an energy diagram of a normal LED.
Figure 3B:
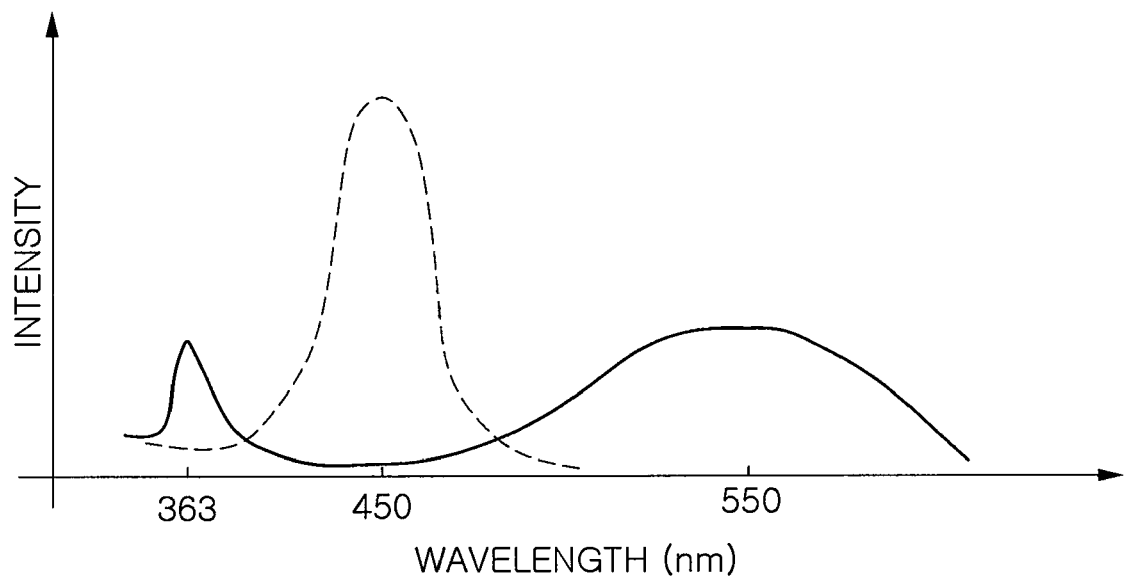
FIG. 3B is a view illustrating a spectrum of light emitted from the LED of FIG. 3A.

FIG. 3A is an energy diagram of a normal LED, and FIG. 3B illustrates a spectrum of light emitted from the LED of FIG. 3A. 'e' and 'h' represent an electron-hole pair e-h excited by the UV irradiation. The generated electron-hole pair e-h decreases an electric field of a space charge region. This has an effect of applying a voltage corresponding to a photo voltage, and thus light emission at the active layer increases.

Referring to FIG. 3B, blue light of about 450 nm and yellow light of about 550 nm are emitted, and thus the LED emits white light as the blue light and the yellow light are mixed together. When a GaN LED is used, a peak appears at about 363 nm.

Figure 4A:
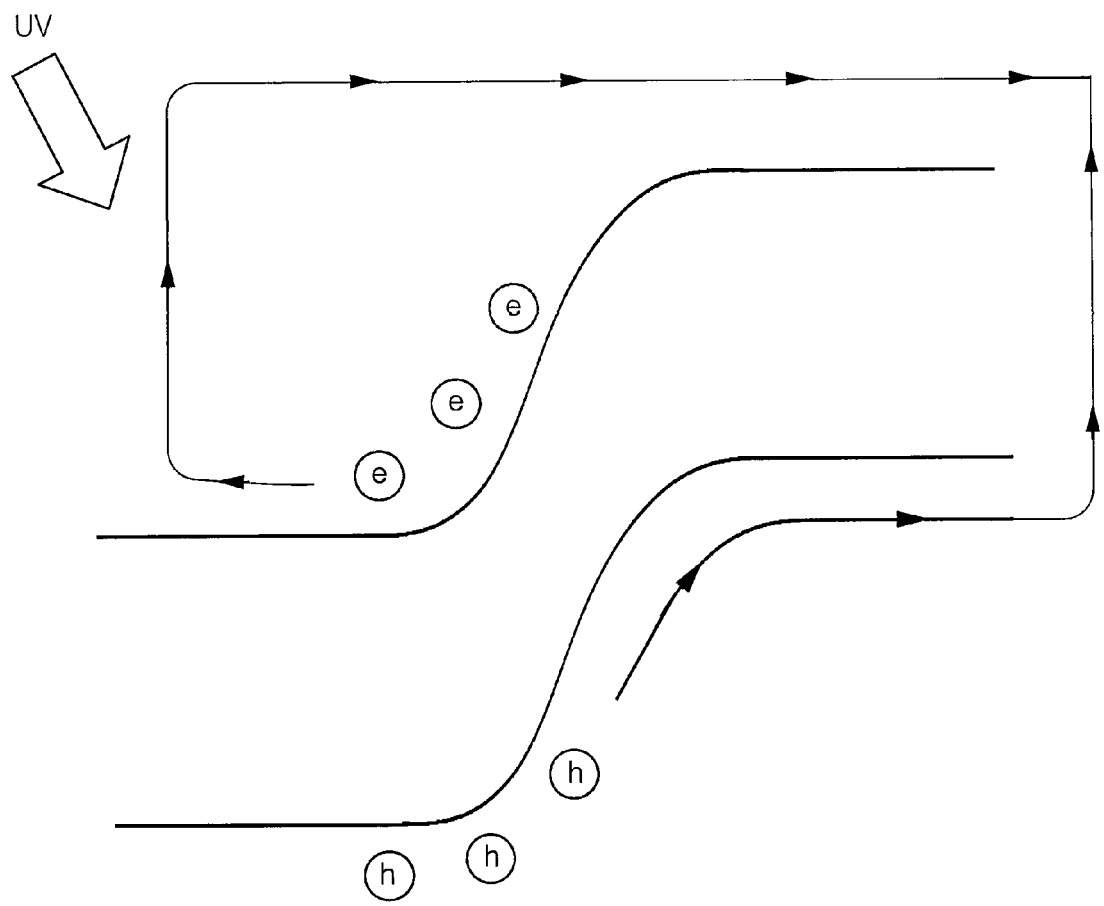
FIG. 4A is an energy diagram of an LED with leakage current.
Figure 4B:
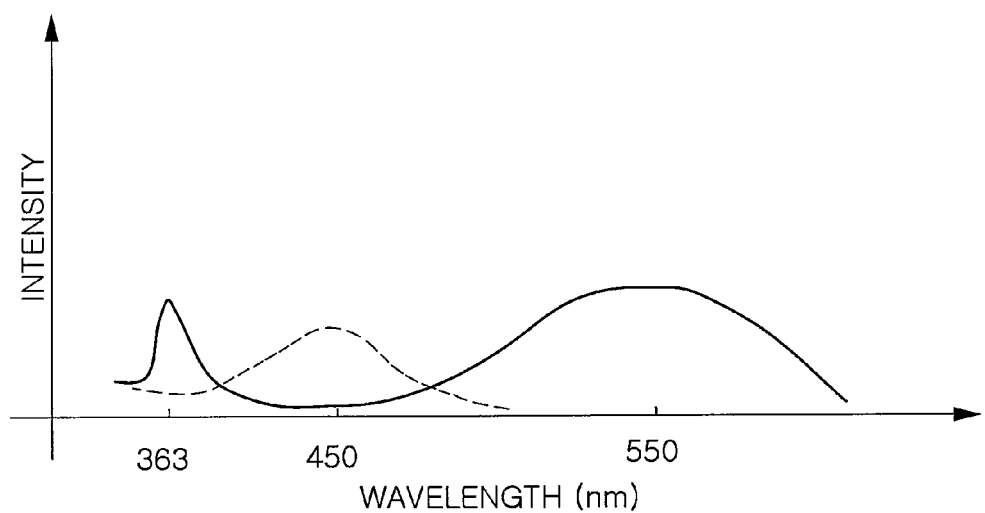
FIG. 4B is a view illustrating a spectrum of light emitted from the LED of FIG. 4A.

Unlike FIG. 3A, FIG. 4A is an energy diagram of an LED where leakage current occurs. FIG. 4B illustrates a spectrum of light emitted from the LED of FIG. 4B. 'e' and 'h' of FIG. 4A represent an electron-hole pair e-h excited by the UV irradiation. The generated electron-hole pair e-h cannot decrease an electric field of a space charge region. This is because the electron 'e' and the hole 'h' irradiatively recombine each other, flowing as the leakage current toward a leakage channel indicated by arrows. Accordingly, a voltage corresponding to a photo voltage cannot be produced, and thus light emission at the active layer does not increase.

Referring to FIG. 4B, yellow light of about 550 nm and blue light of about 450 nm both are emitted. However, since the yellow light has higher intensity than the blue light, the LED emits yellow light on the whole. As shown in FIG. 4B, if a GaN LED is used, a peak appears at about 363 nm.

In this respect, referring to FIG. 2 again, if the LED 120 emits yellow light, the control unit 140 may determine that the LED 120 is defective. For example, a normal blue LED simultaneously emits blue light and yellow light, whereas a defective LED emits only yellow light. As an image of the LED 120 is generated, the control unit 140 obtains color or intensity information of the LED 120. The control unit 140 may be an image processor to process an image.

According to this embodiment, the blue LED is described as an example. However, the present invention is not limited thereto, and it is obvious to those skilled in the art that the present invention is also applicable to a red LED, a green LED or the like. For example, a normal red LED emits mixed light of red and yellow light, and a normal green LED emits mixed light of green and yellow light. If both are defective, they emit yellow or very weak light.

The control unit 140, if the obtained color or intensity information indicates yellow or intensity is weak, determines that the LED is defective. Also, if the color information indicates white or intensity is high, the control unit 140 determines that the LED is normal. The criteria for determining whether the LED 120 is defective can be controlled by changing the UV intensity, and may be widely applied for various kinds of LEDs by variously controlling colors of light and intensity levels thereof, using an image processor.

An LED inspection method using the LED inspection apparatus is provided according to another exemplary embodiment of the present invention. The LED inspection method according to another exemplary embodiment of the present invention includes: emitting UV light to an LED; generating, at an image generation unit, an image of the LED to which the UV light is emitted; obtaining an image of the LED generated from the image generation unit; calculating color or intensity information of the LED from the image; and determining whether or not the LED is defective based on the color or intensity information. The detailed operation is the same as described above with reference to FIGS. 2 through 4.

Figure 5:
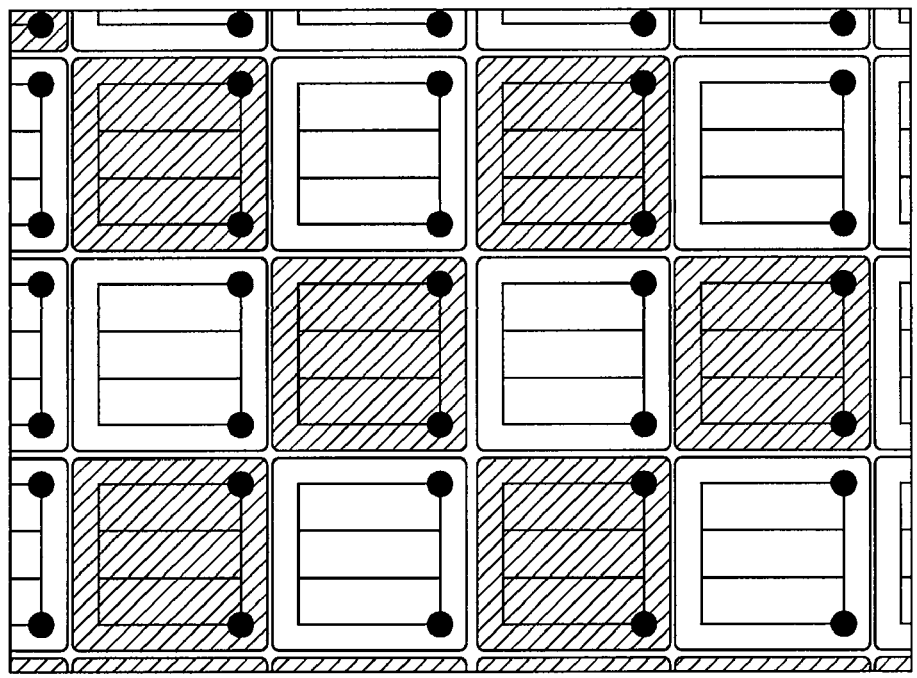
FIG. 5 is an image of an LED obtained through the LED inspection apparatus according to the exemplary embodiment of the present invention.

FIG. 5 is an image of a blue LED array obtained at the LED inspection apparatus according to the embodiment of FIG. 1. The image shows a plurality of blue LEDs. The colors of the LEDs are either white or yellow. If an LED is normal, leakage of an electron-hole pair through a leakage channel does not occur, and the LED emits white light, which is the mixed light of blue and yellow light. However, if the current leakage occurs, an electric field does not change. In this case, the LED emits yellow light and is determined to be defective.

Figure 6:
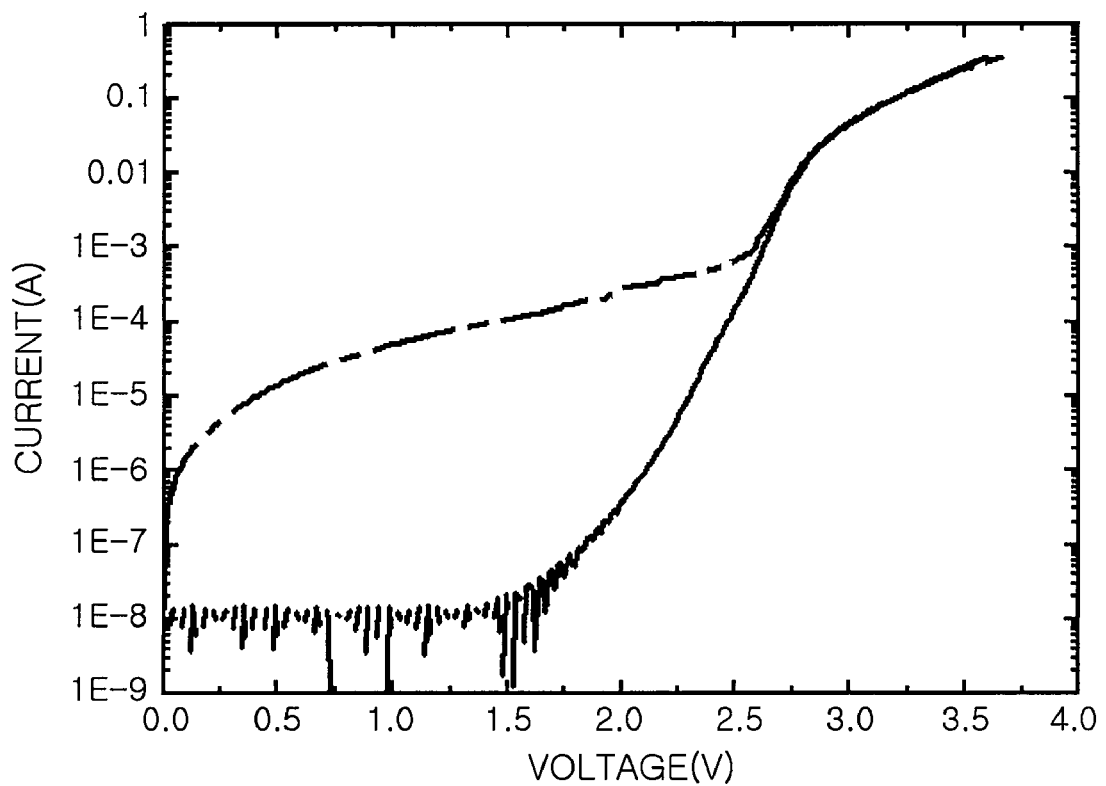
FIG. 6 is a graph showing electrical characteristics of a normal LED and an LED with leakage current.

FIG. 6 is a graph showing electrical characteristics of a normal LED and an LED with current leakage. In FIG. 6, to confirm the result of the determination of the LED inspection apparatus according to the present invention, a related art prober is used to check electrical characteristics of the LED of FIG. 5.

Referring to FIG. 6, an LED, which is white in the image of FIG. 5, does not have an abnormally increasing operating current as indicated by a solid line, whereas an LED which is yellow in the image has an abnormal operating current as indicated by a dotted line.

Accordingly, it is confirmed that the LED inspection apparatus and the LED inspection method according to the present invention have a similar performance to a related art method for checking a defect, while achieving a more efficient and simpler inspection without damaging the LED.

According to the present invention, a defect such as leakage current can be detected without making physical contact with an LED being inspected. Thus, the LED can be protected from the external impact and can be inspected for a shorter period of time.

Also, in an inspection method according to the present invention, the inspection is performed by emitting UV light without applying a voltage. Thus, the inspection can be performed on an LED that does not include a metal contact or the like for an electrical contact. Accordingly, the inspection can be efficiently applied to various processes during an LED manufacturing process.

While the present invention has been shown and described in connection with the exemplary embodiments, it will be apparent to those skilled in the art that modifications and variations can be made without departing from the spirit and scope of the invention as defined by the appended claims.

What is claimed is:

1. A light emitting diode (LED) inspection apparatus comprising:
   an ultraviolet emission unit emitting UV light to an LED;
   an image generation unit generating an image of the LED to which the UV light is emitted; and
   a control unit obtaining color or intensity information of the LED from the image of the LED, and determining, based on the color or intensity information, whether the LED is defective
   wherein the control unit determines that the LED is defective if a color of the LED is yellow.

2. The LED inspection apparatus of claim 1, wherein the image generation unit is a charge-coupled (CCD) camera.

3. The LED inspection apparatus of claim 1, wherein the UV emission unit is one of a UV laser, a UV LED, a xenon arc lamp, a mercury arc lamp, and a xenon mercury arc lamp.

4. The LED inspection apparatus of claim 1, wherein the LED device is one of a blue LED, a red LED and a green LED.

5. The LED inspection apparatus of claim 1, wherein the control unit determines that the LED is defective if an intensity of the LED is weak.

6. The LED inspection apparatus of claim 1, further comprising an LED support spaced apart from the UV emission unit at a predetermined interval, and supporting the LED.

7. The LED inspection apparatus of claim 6, wherein the LED support is movable.

8. A light emitting device (LED) inspection method comprising:
   emitting UV light to an LED;
   generating, at an image generation unit, an image of the LED to which the UV light is emitted;
   obtaining the image of the LED generated from the image generation unit;
   calculating color or intensity information of the LED from the image; and
   determining, based on the color or intensity information, whether the LED is defective
   wherein the determining whether the LED is defective comprises determining, based on the color information, that the LED is defective if a color of the LED is yellow.

9. The LED inspection method of claim 8, wherein the LED is one of a blue LED, a red LED and a green LED.

10. The LED inspection method of claim 8, wherein the determining whether the LED is defective comprises determining, based on the color information, that the LED is defective if an intensity of the LED is weak.

* * * * *